(12) United States Patent
Nakamura et al.

(10) Patent No.: US 11,925,740 B2
(45) Date of Patent: Mar. 12, 2024

(54) BLOOD PROCESSING FILTER AND METHOD FOR PRODUCING BLOOD PROCESSING FILTER

(71) Applicant: ASAHI KASEI MEDICAL CO., LTD., Tokyo (JP)

(72) Inventors: Kazuhiko Nakamura, Tokyo (JP); Tomohisa Yokomizo, Tokyo (JP); Takako Kai, Tokyo (JP)

(73) Assignee: ASAHI KASEI MEDICAL CO., LTD., Tokyo (JP)

( * ) Notice: Subject to any disclaimer, the term of this patent is extended or adjusted under 35 U.S.C. 154(b) by 619 days.

(21) Appl. No.: 17/269,682

(22) PCT Filed: Aug. 29, 2019

(86) PCT No.: PCT/JP2019/034010
§ 371 (c)(1),
(2) Date: Feb. 19, 2021

(87) PCT Pub. No.: WO2020/045592
PCT Pub. Date: Mar. 5, 2020

(65) Prior Publication Data
US 2021/0316049 A1    Oct. 14, 2021

(30) Foreign Application Priority Data

Aug. 30, 2018  (JP) .................. 2018-161285

(51) Int. Cl.
*A61M 1/02* (2006.01)
*A61M 1/36* (2006.01)

(52) U.S. Cl.
CPC ........ *A61M 1/3635* (2014.02); *A61M 1/0218* (2014.02); *A61M 1/0281* (2013.01); *A61M 2202/0028* (2013.01); *A61M 2202/0439* (2013.01); *A61M 2205/75* (2013.01)

(58) Field of Classification Search
CPC .............. A61M 1/3635; A61M 1/0218; A61M 1/0281; A61M 2202/0028;
(Continued)

(56) References Cited

U.S. PATENT DOCUMENTS 7,438,821 B2 *  10/2008  Yokomizo ........... A61M 1/0222
                                                           210/741
2006/0184085 A1 *  8/2006  Kimura ............... A61M 1/3633
                                                           604/6.03
(Continued)

FOREIGN PATENT DOCUMENTS

CN      101098704       1/2008
CN      202554574       11/2012
(Continued)

OTHER PUBLICATIONS

International Search Report issued in Patent Application No. PCT/JP2019/034010, dated Oct. 15, 2019 and English language translation thereof.

(Continued)

*Primary Examiner* — Nicholas J. Weiss
*Assistant Examiner* — Brandon W. Levy
(74) *Attorney, Agent, or Firm* — GREENBLUM & BERNSTEIN, P.L.C.

(57) ABSTRACT

A blood processing filter includes a container having 2 ports respectively functioning as an inlet for a liquid to be processed and as an outlet for the processed liquid, and a filtration medium filled in the container, wherein an airflow resistance of the filtration medium is 55.0 kPa·s/m or more and less than 85.0 kPa·s/m, the filtration medium includes a filter material A having an airflow resistance per unit basis weight of 0.01 kPa·s·m/g or more and less than 0.04 kPa·s·m/g and a filter material B having an airflow resistance per unit basis weight of 0.04 kPa·s·m/g or more, at least a
(Continued)

part of the filter material A is disposed on a side closer to the inlet for a liquid to be processed than the filter material B, and a sum of airflow resistances of the filter material A is 6.0 kPa·s/m or more.

6 Claims, 1 Drawing Sheet

(58) Field of Classification Search
CPC ...... A61M 2202/0439; A61M 2205/75; A61M 2207/00; A61M 1/3633; A61M 1/0222; A61M 1/0231; A61M 1/16; A61M 1/3636; B01D 2239/0421; B01D 2239/065; B01D 39/1615; B01D 39/1669; B01D 39/1692; B01D 2239/1291; B01D 39/08; B01D 39/1623; B01D 39/2017; B01D 2239/0492; B01D 2239/0618; B01D 2239/0622
See application file for complete search history.

(56) References Cited

U.S. PATENT DOCUMENTS

| | | |
|---|---|---|
| 2008/0110829 A1 | 5/2008 | Kobayashi |
| 2012/0067810 A1 | 3/2012 | Yokomizo et al. |
| 2016/0136554 A1 | 5/2016 | Swaminathan et al. |
| 2018/0185562 A1 | 7/2018 | Shimada |

FOREIGN PATENT DOCUMENTS

| | | |
|---|---|---|
| CN | 202699682 | 1/2013 |
| CN | 107708760 | 2/2018 |
| JP | 2-203909 | 8/1990 |
| JP | 9-140787 | 6/1997 |
| JP | 2003-180822 | 7/2003 |
| JP | 2007-050013 | 3/2007 |
| JP | 2012-183237 | 9/2012 |
| WO | 2006/073106 | 7/2006 |
| WO | 2012/039400 | 3/2012 |
| WO | 2013/110694 | 8/2013 |
| WO | 2016/204297 | 12/2016 |

OTHER PUBLICATIONS

International Preliminary Report on Patentability issued in PCT/JP2019/034010, dated Mar. 2, 2021 and English language translation thereof.

European Search Report received in EP Appl No. 19855802.5, dated Feb. 10, 2022.

* cited by examiner

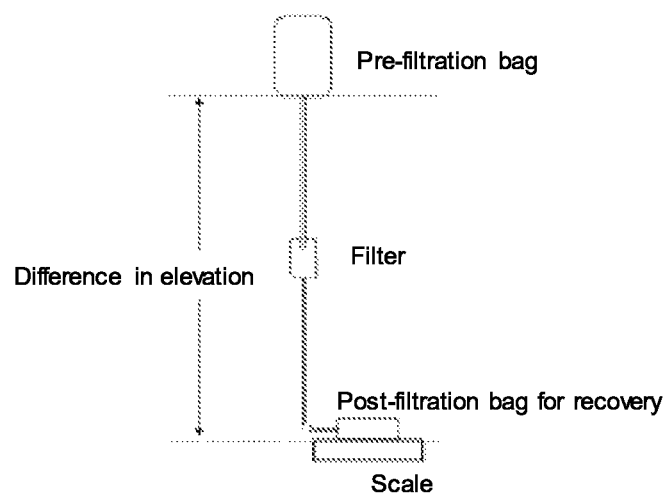

BLOOD PROCESSING FILTER AND METHOD FOR PRODUCING BLOOD PROCESSING FILTER

TECHNICAL FIELD

The present invention relates to a blood processing filter for removing undesirable components such as aggregates and leukocytes from a liquid containing blood components or blood, and to a method for producing the blood processing filter.

Particularly, the present invention relates to a blood processing filter suitable as a blood processing filter used for the purpose of removing microaggregates and leukocytes, which are likely to cause side effects, from whole blood preparations, erythrocyte preparations, thrombocyte preparations, blood plasma preparations and the like for blood transfusion.

BACKGROUND ART

Whole blood collected from donors has been used as the source for blood component preparations such as an erythrocyte preparation, a thrombocyte preparation, and a blood plasma preparation. However, whole blood contains undesirable components such as microaggregates and leukocytes, which are likely to cause various blood transfusion side effects. For this reason, it is common to remove undesirable components after drawing blood or before using a blood component preparation.

For the method for removing undesirable components such as leukocytes from whole blood and blood component preparations, filter methods have been widely used due to a simple operation and a low cost, the filter methods involving use of a blood processing filter including a filtration medium made of fiber assemblies such as nonwoven fabrics or a porous material having continuous pores.

It is considered that the mechanism of leukocyte removal by the filter methods is predominantly due to the adhesion or adsorption of leukocytes onto the surface of the filtration medium when they come in contact with such a surface. Accordingly, for enhancing the capability to remove leukocyte, attempts have been made so that the contact frequency of the filtration medium and leukocytes is increased, specifically, fiber diameters of the fiber or pore diameters of the porous material forming the filtration medium are reduced or the bulk density is increased thereby to increase the surface area of the filtration medium per unit volume to enhance the capability to remove leukocyte (Patent Literature 1). These methods can enhance the capability to remove leukocyte; however a pressure loss caused by the filtration medium when processing blood becomes larger at the same time, which results in a reduced flow rate and consequently a longer filtration time.

For the means for reducing the pressure loss, the improvement in blood wettability of the filtration medium by applying surface modification or surface treatment to the filtration medium is studied (Patent Literature 2). These methods can reduce the pressure loss to reduce the filtration time extension, but it is difficult for these methods to maintain good capability to remove leukocyte.

CITATION LIST

Patent Literature

Patent Literature 1: Japanese Patent Laid-Open No. 2-203909
Patent Literature 2: Japanese Patent Laid-Open No. 2007-50013

SUMMARY OF INVENTION

Technical Problem

An object of the present invention is to provide a blood processing filter capable of solving two problems which are difficult to be solved simultaneously, i.e., of achieving both a high capability to remove leukocyte and filtration time reduction.

Solution to Problem

The present inventors have conducted extensive studies to solve the above problems and found that a blood processing filter having both high capability to remove leukocyte and high blood flow performance can be obtained when a filtration medium is composed of two kinds of filter materials having different airflow resistances per unit basis weight, that is, comparatively coarse filter materials and comparatively dense filter materials, these filters being disposed in a container in such a way that the coarse filter materials are positioned at the upper stream side (an inlet side of a liquid to be processed) than the dense filter materials, even with an airflow resistance of the filtration medium being 55.0 kPa·s/m or more and less than 85.0 kPa·s/m; and the present invention has been thus accomplished.

Specifically, the present invention relates to the followings.

[1]

A blood processing filter comprising:

a container having 2 ports respectively functioning as an inlet for a liquid to be processed and as an outlet for the processed liquid, and a filtration medium filled in the container, wherein an airflow resistance of the filtration medium is 55.0 kPa·s/m or more and less than 85.0 kPa·s/m, the filtration medium comprises a filter material A having an airflow resistance per unit basis weight of 0.01 kPa·s·m/g or more and less than 0.04 kPa·s·m/g and a filter material B having an airflow resistance per unit basis weight of 0.04 kPa·s·m/g or more, at least a part of the filter material A is disposed on a side closer to the inlet for a liquid to be processed than the filter material B, and a sum of the airflow resistances of the filter material A that is disposed on the side closer to the inlet for a liquid to be processed than the filter material B is 6.0 kPa·s/m or more.

[2]

The blood processing filter according to [1] comprising:

a plurality of kinds of the filter material A, wherein when a filter material having the lowest airflow resistance per unit basis weight among a plurality of kinds of the filter material A is designated as a filter material A', at least a part of the filter material A' is disposed on the side closer to the inlet for a liquid to be processed than the filter material B, and a sum of the airflow resistances of the filter material A' that is disposed on the side closer to the inlet for a liquid to be processed than the filter material B is 6.0 kPa·s/m or more.

[3]

The blood processing filter according to [1] or [2], wherein the airflow resistance of the filtration medium is 55.0 kPa·s/m or more and less than 70.0 kPa·s/m, and the sum of the airflow resistances of the filter material A that is disposed on the side closer to the inlet for a liquid to be processed than the filter material B is 12.0 kPa·s/m or more and less than 32.0 kPa·s/m.

[4]

The blood processing filter according to any of [1] to [3], wherein a critical wet surface tension (CWST) of the filter material B is 80 mN/m or more and 90 mN/m or less.

[5]

The blood processing filter according to [1] or [2], wherein the airflow resistance of the filtration medium is 70.0 kPa·s/m or more and less than 85.0 kPa·s/m, and the sum of the airflow resistances of the filter material A that is disposed on the side closer to the inlet for a liquid to be processed than the filter material B is 24.0 kPa·s/m or more.

[6]

A method for producing the blood processing filter according to any of [1] to [5] comprising:

the step of providing a filter material A and a filter material B, and the step of laminating at least a part of the filter material A to the filter material B to make a laminated product.

Advantageous Effects of Invention

The blood processing filter according to the present invention can achieve a high capability to remove leukocyte and filtration time reduction simultaneously.

BRIEF DESCRIPTION OF DRAWINGS

FIG. 1 is a schematic drawing of the experimental apparatus used for the leukocyte removing performance test of the blood processing filters carried out in Examples.

DESCRIPTION OF EMBODIMENTS

Hereinafter, an embodiment to carry out the present invention (hereinafter, referred to as the present embodiment) will be described in detail. The present invention is not limited to the following embodiment and can be carried out in various modifications within the scope of the gist.

The blood processing filter of the present embodiment comprises a container having 2 ports respectively functioning as an inlet for a liquid to be processed and as an outlet for the processed liquid, and a filtration medium filled in the container.

The container containing the filtration medium is not particularly limited as long as it has 2 ports respectively functioning as an inlet for a liquid to be processed (a liquid or blood containing blood components) and as an outlet for the processed liquid (the liquid (blood) from which undesirable components such as leukocytes have been removed), and a common container used for various liquid processing filters can be used.

The shape thereof (the shape of the main body) can be a shape in accordance with the shape of the filtration medium. For example, when the filtration medium has a shape of flat plate, the container may have, for example, a flat shape of a polygon, such as quadrangle or hexagon, or a shape having a curved line, such as circle and oval, and when the filtration medium is cylindrical, the container can be cylindrical. The material therefor is not limited and can be a hard material or a flexible (sheet-like) material.

The filtration medium is disposed in the container so that the internal space of the container is separated into the inlet-side and the outlet-side.

In the present embodiment, an airflow resistance of the filtration medium (the sum of airflow resistances of all the filter materials composing the filtration medium; also referred to as the total airflow resistance) is 55.0 kPa·s/m or more and less than 85.0 kPa·s/m. When an airflow resistance of the filtration medium is within this range, the leukocyte removing performance to be expected of a blood processing filter can be delivered in a suitable filtration time. The airflow resistance of the filtration medium is the sum of airflow resistances of all the filter materials composing the filtration medium, which is also referred to as the total airflow resistance.

The airflow resistance (kPa·s/m) used herein is a value measured as a differential pressure caused when air at a constant air flow is allowed to pass through a sample (filtration medium or filter material(s)), and, specifically, is a value of a pressure loss (kPa·s/m) measured when air is ventilated for 10 seconds through a filter material placed on a vent hole of an air permeability tester (for example, KES-F8-AP1 manufactured by KATO TECH CO., LTD.). The size of a filter material for the measurement may be such that no gap is made at the vent hole of the air permeability tester.

The value of an airflow resistance can be specifically measured by the method described in Examples.

The airflow resistance per unit basis weight of a filter material of the present embodiment is a value obtained by dividing an airflow resistance (kPa·s/m) of a filter material by a basis weight (g/m$^2$) of the filter material.

The basis weight (g/m$^2$) used herein is a value obtained by measuring an area and a mass of a nonwoven fabric cut to an arbitrary size larger than 5 cm$^2$ or more so as to avoid measuring a local value of the weight of the filter material, and calculating using the following formula.

Basis Weight=mass of filter material (g)/area of filter material (m$^2$)

A high airflow resistance per unit basis weight means that air is less likely to pass through it, and, for example, when a filtration medium is made of fibers, it suggests that the fibers are interwoven in a dense or uniform state. For this reason, it is commonly difficult for a liquid to flow through a filtration medium having a high airflow resistance per unit basis weight, and clogging with blood cells increases, thereby resulting in a tendency to reduce a processing speed.

On the other hand, a low airflow resistance per unit basis weight means that air is more likely to pass through it, and, for example, when a filtration medium is made of fibers, it suggests that the fibers are interwoven in a coarse or non-uniform state. For this reason, it is commonly easy for a liquid to flow through a filtration medium having a low airflow resistance per unit basis weight, but, as a result, the number of contacts with leukocytes decreases, thereby resulting in a tendency to reduce the leukocyte removing performance.

For the measurement of an airflow resistance and a basis weight of a filter material integrated in the filtration medium (a product), the product is disassembled to take out the filter materials composing it, and an airflow resistance and a basis weight of each filter material are measured.

Specifically, the filtration medium is obtained by detaching from the container at near the margins of filtering area.

Subsequently, when the filtration medium is composed of a plurality of sheets of filter materials, each of them is peeled to obtain individual sheets of the filter material.

In the present embodiment, the filter material refers to, among a plurality of layers composing the filtration medium, an integral sheet-like material separable from others and may be a single layer or be composed of a plurality of layers.

In the present embodiment, the filtration medium includes two kinds of filter materials having different airflow resistances per unit basis weight. Specifically, the filtration medium includes a filter material A having an airflow resistance per unit basis weight of 0.01 kPa·s·m/g or more and less than 0.04 kPa·s·m/g and a filter material B having an airflow resistance per unit basis weight of 0.04 kPa·s·m/g or more.

A single sheet of the filter material A may be included, or a plurality of sheets of the filter material A may be included. The same is also applied to the filter material B.

Also, a single kind of the filter material A may be included, or a plurality of kinds of the filter material A may be included. The same is also applied to the filter material B.

Furthermore, in the present embodiment, the filtration medium may include filter materials other than the above filter material A or B, that is, filter materials having an airflow resistance per unit basis weight of less than 0.01 kPa·s·m/g.

The form of each filter material included in the filtration medium is not particularly limited as long as it is a form having pores capable of filtering blood and the respective airflow resistance per unit basis weight, and various porous materials can be used. In particular, fibrous media such as knitted fabrics, woven fabrics, and nonwoven fabrics made of natural fibers, synthetic fibers, or glass fibers, porous membranes, materials of a spongy structure having three-dimensional network continuous pores are preferable.

The material for filter materials is not particularly limited as long as it is less likely to damage blood cells, and various materials can be used such as organic polymer materials, inorganic polymer materials and metals. Of these, organic polymer materials are preferable base materials in view of good processability for cutting, for example. Examples of the organic polymer material include, but not limited to, polyester, polyolefin, polyacrylonitrile, polyamide, polystyrene, polymethylmethacrylate, polyvinyl fluoride, polyurethane, polyvinyl alcohol, polyvinyl acetal, polysulfone, polyvinylidene fluoride, polytrifluorochlorovinyl, vinylidene fluoride-tetrafluoroethylene copolymers, polyethersulfone, polyacrylate, butadiene-acrylonitrile copolymers, polyether-polyamide block copolymers, ethylene-vinylalcohol copolymers, cellulose, and cellulose acetate. Of these, polyester and polyolefin are preferable, and polyester is particularly preferable.

The method for controlling an airflow resistance of the filter materials is not limited. For example, when a filter material is made of a nonwoven fabric, an airflow resistance thereof can be adjusted by changing a fiber diameter and a density of the nonwoven fabric forming the filter material. It is considered that, among nonwoven fabrics having the same basis weight or density, a nonwoven fabric having a smaller fiber diameter has a larger airflow resistance due to, for example, an increase in the specific surface area. Also, it is considered that, among nonwoven fabrics having the same fiber diameter, a nonwoven fabric having a larger density has a larger airflow resistance due to, for example, a reduced pore diameter.

The fiber diameter and the density of a nonwoven fabric can be arbitrarily adjusted by controlling conditions when producing the nonwoven fabric. An example of such a method for producing a nonwoven fabric by which the fiber structure of a nonwoven fabric is easily adjusted is a melt blown method, and a nonwoven fabric having an intended airflow resistance can be obtained by considering spinning factors such as a resin viscosity, a melting temperature, a discharge per single hole, a hot gas temperature, a hot gas pressure, and a distance between spinnerets and a collection screen. For the method for producing a filter material (nonwoven fabric) having a suitable airflow resistance, suitable production conditions can be determined based on known information (for example, Non Patent Literature: "Fushokufu no Kiso to Oyo (in Japanese)" ("Foundation and Application of Nonwoven fabric"), P. 119-127, published in Aug. 25, 1993, General Incorporated Association Japan Textile Machinery Association) by taking into consideration of the above-described technical ideas and the selection of production process.

In the present embodiment, the melt blown method, for example, can provide polybutylene terephthalate (PBT) nonwoven fabrics having different airflow resistances per unit basis weight by controlling the following conditions. The spinning condition in the melt blown method include the number of spinnerets of a melt blown die, a discharge per single hole, and a hot air amount, and these can be set as desired.

The number of spinnerets of a melt blown die can be typically set to be 5 holes/cm or more and 30 holes/cm or less.

The discharge per single hole can be typically set to be 0.12 g/(min-hole) or more and 0.20 g/(min-hole) or less.

The hot air amount can be typically set to be 100 Nm$^3$/hr or more and 400 Nm$^3$/hr or less.

According to the study by the present inventors, it has been revealed that the leukocyte removing performance is more enhanced when the filtration medium is composed of two kinds of filter materials having different airflow resistances per unit basis weight, specifically, a filter material having an airflow resistance per unit basis weight of 0.01 kPa·s·m/g or more and less than 0.04 kPa·s·m/g (filter material A) and a filter material having an airflow resistance per unit basis weight of 0.04 kPa·s·m/g or more (filter material B), than when the filtration medium is made of a single kind of filter material, even when a value of the airflow resistance as the filtration medium is the same.

The airflow resistance per unit basis weight of the filter material A herein is more preferably 0.03 kPa-m-s/g or more and 0.04 kPa-m-s/g or less.

The airflow resistance per unit basis weight of the filter material B herein is more preferably 0.08 kPa-m-s/g or less.

Further, the filtration time increases or reduces in accordance with the disposition of these filter materials in the blood processing filter. Specifically, it has been revealed that when the coarse filter material A is disposed in the filtration medium in such a way as to be positioned at the upper stream side (the inlet side for a liquid to be processed) than the dense filter material B (when a plurality of sheets of the filter material B are included, a filter material B positioned at the uppermost stream thereamong), the filtration time can be shortened while the leukocyte removing performance remains unchanged.

Thus, when the filter materials A and B are disposed as described, both the short filtration time and the high leukocyte removing performance can be achieved, which has been considered to be difficult.

The reason is not clear why the enhanced leukocyte removing performance and the shortened filtration time can be provided when the coarse filter material A and the dense filter material B are used in combination at the specific disposition, but the following is presumed: clogging by over adsorption of leukocytes and a reduced flow rate are not caused in the filter material A disposed at the upstream, and leukocytes are gradually captured in the direction of thickness of the filtration medium; and thus, in the filter material B disposed at the downstream, leukocytes can be efficiently removed from blood in which a leukocyte concentration and an aggregate content are reduced. However, the mechanism is not bound to this.

Taking into consideration the expectation that the use of a coarse filter material reduces the removing performance due to a reduced number of contacts with leukocytes, it could have been totally unexpected that the simple disposition of the coarse filter material A at the upstream can shorten the filtration time and further does not affect the leukocyte removing performance.

When a plurality of sheets of the filter material A are included in the filtration medium, all of them do not need to be positioned at the upper stream side than the filter material B, and at least a part thereof can be positioned at the upper stream side than the filter material B.

It is, of course, preferable that a certain amount or more of the filter material A should be disposed at the upper stream side than the filter material B in view of shortening the filtration time, and specifically, the sum of airflow resistances of the filter material A that is disposed on the upper stream side than the filter material B is preferably 6.0 kPa·s/m or more.

The sum of airflow resistances of the filter material A that is disposed on the upper stream side than the filter material B is more preferably 8.0 kPa·s/m or more, further preferably 10.0 kPa·s/m or more, and furthermore preferably 12.0 kPa·s/m or more.

On the other hand, the sum of airflow resistances of the filter material A that is disposed on the upper stream side than the filter material B is preferably 80 kPa·s/m or less. When the sum of airflow resistances of the filter material A that is disposed on the upper stream side than the filter material B is 80 kPa·s/m or less, a mass of the filter material A that is disposed on the upstream side is not too large and a mass of the filtration medium can be reduced. This reduces a blood loss in the filter after filtration and sufficient amount of blood recovered can thus be expected, which is preferable.

When an airflow resistance of the filtration medium herein is less than 70.0 kPa·s/m, the sum of airflow resistances of the filter material A that is disposed on the upper stream side than the filter material B is the most preferably 12.0 kPa·s/m or more and less than 32.0 kPa·s/m.

On the other hand, when an airflow resistance of the filtration medium is 70.0 kPa·s/m or more, the sum of airflow resistances of the filter material A that is disposed on the upper stream side than the filter material B is preferably 6 kPa·s/m or more, and the most preferably 24.0 kPa·s/m or more. When an airflow resistance of the filtration medium is 70.0 kPa·s/m or more, the sum of airflow resistances of the filter material A that is disposed on the upper stream side than the filter material B is not particularly limited and is preferably 6 kPa·s/m or more and 44 kPa·s/m or less, and more preferably 24 kPa·s/m or more and 44 kPa·s/m or less.

The airflow resistance of the filtration medium having such values is likely to enable the filtration time to be more shortened.

It is not clear why preferable values in the sum of airflow resistances of the filter material A that is disposed on the upper stream side than the filter material B vary depending on the value of airflow resistance of the filtration medium, but the following is presumed: in the leukocyte removing process in which the filtration is commonly carried out using a natural difference in elevation as a driving force, a low airflow resistance of the filtration medium causes a high flow rate of blood passing through filter materials, and the over adsorption of leukocytes in the dense filter material B is thus less likely to occur, whereby the sum of airflow resistances of the filter material A can be reduced low.

To the contrary, a high airflow resistance of the filtration medium causes a low flow rate of blood passing through the filter materials, and this induces the over adsorption of leukocytes in the dense filter material B. Thus, it is conceivable that the sum of airflow resistances of the filter material A needs to be increased to shorten the filtration time without affecting the leukocyte removal.

Additionally, when a plurality of kinds of the filter material A are included, any of the filter material A can be disposed on the upper stream side than the filter material B. However, when a filter material having the lowest airflow resistance (most coarse) per unit basis weight among the filter material A is designated as a filter material A', the filter material A' is preferably present at the upper stream than the filter material B.

In this case, the sum of airflow resistances of the filter material A' that is disposed on the upper stream side than the filter material B is preferably 6.0 kPa·s/m or more, 8.0 kPa·s/m or more, 10.0 kPa·s/m or more, or 12.0 kPa·s/m or more.

Each of the nonwoven fabrics composing the filter elements can be surface modified by a known technique such as coating, chemical treatment, or radiation treatment for the purpose of controlling the preferential segregation of blood cells and hydrophilicity of the surface. For coating, at least a part of the surface of a filter substrate is coated with a polymer to provide a polymer coating layer thereby to hydrophilize or hydrophobilize the surface thereof.

The hydrophilic polymer is not particularly limited but it is preferable to use a polymer having a nonionic hydrophilic group and a basic nitrogen-containing functional group. When the filter material surface is hydrophilized with such a polymer, the wettability of the filter material is improved, and the blood cell capture performance is also enhanced by introducing a chargeable functional group, which are preferable.

In the present embodiment, examples of the nonionic hydrophilic group include a hydroxyl group and an amide group.

Examples of the monomer containing a nonionic hydrophilic group include monomers containing the above-mentioned hydroxyl group and amide group such as 2-hydroxyethyl(meth)acrylate, 2-hydroxypropyl(meth)acrylate, vinyl alcohol (polymerized as vinyl acetate and then hydrolyzed), (meth)acrylamide, and N-vinylpyrrolidone.

Examples of the nonionic hydrophilic group include a polyethylene oxide chain, in addition to the above hydroxyl group and the amide group. Examples of the monomer containing a polyethylene oxide chain include alkoxypolyethyleneglycol(meth)acrylates such as methoxyethyleneglycol(meth)acrylate, methoxydiethyleneglycol(meth)acrylate, methoxytriethyleneglycol(meth)acrylate, and methoxytetraethyleneglycol(meth)acrylate.

Of the above monomers, 2-hydroxyethyl(meth)acrylate is preferably used because of availability, ease of handling when polymerizing, and performance when blood is allowed to flow.

Examples of the basic nitrogen-containing functional group include a primary amino group, a secondary amino group, a tertiary amino group, a quaternary ammonium group, and nitrogen-containing aromatic groups such as a pyridine group and an imidazole group.

Examples of the monomer containing a basic nitrogen-containing functional group include allylamine; derivatives of (meth)acrylate such as dimethylaminoethyl(meth)acrylate, dimethylaminopropyl(meth)acrylate, and 3-dimethylamino-2-hydroxyl(meth)acrylate; styrene derivatives such as p(para)-dimethylaminomethylstyrene and p-dimethylaminoethylstyrene; vinyl derivatives of nitrogen-containing aromatic compounds such as 2-vinylpiridine, 4-vinylpiridine, and 4-vinylimidazole; and derivatives in the form of a quaternary ammonium salt obtained from the above vinyl compounds using alkyl halide or the like.

Of the above monomers, dimethylaminoethyl(meth)acrylate and diethylaminoethyl(meth)acrylate are preferably used because of availability, ease of handling when polymerizing, and performance when blood is allowed to flow.

In the present embodiment, it is preferable that a content of the basic nitrogen atom in the above-mentioned polymer coating layer formed by a polymer be 0.2 mass % or more and 8.0 mass % or less. This is likely to enhance the wettability of a nonwoven fabric to blood.

When a content of the basic nitrogen atom is 0.2 mass % or more, the wettability of the filter to blood increases and the initial soak of blood into the filtration medium is easier, thereby resulting in a tendency to shorten the filtration time. Further, a so-called one-sided flow, which is a condition of blood passing only through a part of the filtration medium where is easy to flow without using throughout the entire filtration medium, can be reduced and consequently the filtration time is easily shortened to enhance the capability to remove leukocyte.

When a content of the basic nitrogen atom is 8.0 mass % or less, hemolysis of red blood cells caused by clogging of a coating agent among the fibers is likely to be reduced.

A content of the basic nitrogen atom for a whole blood preparation is preferably 0.2 mass % or more and 8.0 mass % or less, and more preferably 0.3 mass % or more and 7.0 mass % or less. A content of the basic nitrogen atom for a thrombocyte preparation is preferably 0.2 mass % or more and 4.0 mass % or less in view of enhancing the preferential segregation between leukocytes and platelets.

A content of the basic nitrogen atom can be calculated by immersing a filter material in a solvent such as EtOH to extract a coating polymer and measuring a nitrogen content of the extract evaporated to dryness by the elemental analysis or the like. The presence or absence of the nonionic hydrophilic group and the basic nitrogen-containing functional group can be determined by the surface analysis of the filter material using attenuated total reflection infrared spectroscopy (ATR-IR) or Time-of-Flight Secondary Ion Mass Spectrometry (TOF-SIMS).

In the present embodiment, a critical wet surface tension (CWST) of the filter material (when the filter material has a coating layer, the material coated with the coating layer) is preferably 70 mN/m or more and 110 mN/m or less. A nonwoven fabric having such a critical welt surface tension can effectively capture undesirable components such as leukocytes while assuring stable wettability to blood.

Further, in the present embodiment, it is particularly preferable that a CWST of the filter material B be 80 mN/m or more and 90 mN/m or less. In this case, undesirable components such as leukocytes can be effectively captured by the filter material B. This raises a concern for an increase in the clogging by blood cells in the dense filter material B to thereby reduce a processing speed; however, the disposition of the coarse filter material A at the upstream of the dense filter material B enables both of favorable leukocyte removing performance and filtration time. The reason therefor is presumed as follows: leukocytes are gradually captured in the direction of thickness of the filtration medium in the filter material A disposed at the upstream; and thus, in the filter material B disposed at the downstream, leukocytes can be efficiently removed from blood in which a leukocyte concentration and an aggregate content are reduced. Thus, it is conceivable that undesirable components such as leukocytes can be effectively captured without extending the filtration time.

Hereinafter, a measurement method of a CWST value will be described.

A plurality of solutions having different known surface tensions are provided by purchasing or preparing. The surface tensions of the provided solutions are measured in Standard atmospheres for conditioning and testing (JIS K 7100) at a temperature of 23° C. and a relative humidity of 50% using an automatic surface tensiometer (Kyowa Interface Science Co., Ltd., Wilhelmy Plate Method).

Ten drops, 10 μL per drop, of the solution having a certain surface tension are quietly dripped on a leveled sample and allowed to stand for 10 minutes. When a contact angle between the filtration medium and the solution becomes 90 degree or less, it is determined that the dripped solution have infiltrated, and when 9 drops or more out of 10 drops have infiltrated, it is determined the filtration medium have been infiltrated with the solution having such a surface tension. When 2 drops or more out of 10 drops do not infiltrate, it is determined that the filtration medium have not been infiltrated with the solution having such a surface tension.

The same operation is repeated using a solution having a surface tension 2 mN/m lower than that of the previously used solution when the filtration medium was not infiltrated or using a solution having a surface tension 2 mN/m higher than that of the previously used solution when the sample infiltrated, thereby to determine the maximum value of a surface tension of the solution that infiltrates and the minimum value of a surface tension of the solution that does not infiltrate, and an average value thereof is taken as the CWST value.

When the measurement is carried out at a temperature different from the temperature of 23° C. and/or a humidity different from the relative humidity of 50%, a CWST value at a temperature of 23° C. and a relative humidity of 50% is calculated using a conversion table, if available.

The blood processing filter of the present embodiment can be produced by a production method comprising the step of preparing the filter material A and the filter material B and the step of laminating at least a part of the filter material A to the filter material B to make a laminated product.

The blood processing filter of the present embodiment comprises a container having 2 ports respectively functioning as an inlet for a liquid to be processed and as an outlet for the processed liquid, and thus the production method of the present embodiment can include the step of putting the laminated product obtained as described above in the above container. At this time, a layer of the filter material A in the laminated product is disposed on the side closer to the inlet for a liquid to be processed of the container.

EXAMPLE

Hereinafter, the present invention will be described in further detail by way of Examples but is not limited to the following Examples.

Each of the physical properties of filter materials and blood processing filters in Examples and Comparative Examples were measured by the following methods.

(Measurement of Airflow Resistance of Filtration Medium)

A sample (filtration medium) having a size of 5 cm×20 cm was placed on a vent hole (a vent hole area 2 $\pi cm^2$ (T 1.414 cm)) of an air permeability tester (KES-F8-AP1 manufactured by KATO TECH CO., LTD.), and a pressure loss (kPa·s/m) (a pressure difference between both sides partitioned with the sample) caused when air was allowed to ventilate for about 10 seconds at 8 $\pi cm^3$/s was measured, which was taken as an airflow resistance.

(Measurement of Basis Weight of Filter Material)

A sample having a size of 5 cm×20 cm was cut out from a filter material and placed on a scale (Model No: XP205, manufacturer: METTLER TOLEDO) to measure a mass thereof. A basis weight of the filter material was calculated from the found value according to the following formula.

Basis Weight=mass of filter material (g)/area of the filter material ($m^2$)

(Measurement of Airflow Resistance Per Unit Basis Weight of Filter Material)

A sample (filter material) having a size of 5 cm×20 cm was placed on a vent hole of the above-mentioned air permeability tester (KES-F8-AP1 manufactured by KATO TECH CO., LTD.), and a pressure loss (kPa·s/m) caused when air was allowed to ventilate for about 10 seconds at 8 $\pi cm^3$/s was measured, which was taken as an airflow resistance. The found value was divided by the basis weight of the sample (g/$m^2$) measured in advance to determine an airflow resistance per unit basis weight.

(Leukocyte Removing Performance of Blood Processing Filter)

An erythrocyte preparation prepared in accordance with the European standard (the Guide to the Preparation, Use and Quality Assurance of Blood Components, 19$^{th}$ edition (2017)), was used as a blood preparation, and it was filtered with blood processing filters of Examples and Comparative Examples using a natural difference in elevation of 110 cm and recovered thereby to obtain filtered blood preparations. The difference in elevation herein was defined, as shown in FIG. 1, from the lowest part of a pre-filtration bag containing the erythrocyte preparation to the lowest part of a post-filtration bag for recovering the erythrocyte preparation (to the top of a scale in the illustration of FIG. 1).

Subsequently, a leukocyte removing performance was calculated in accordance with the following calculation formula.

Leukocyte removing performance=−log [(leukocyte concentration in filtered blood preparation)/(leukocyte concentration in pre-filtration blood preparation)]

The measurement of a leukocyte concentration in the blood preparation before and after filtration was carried out using a white blood cell counting kit "LeucoCOUNT" manufactured by Becton, Dickinson and Company (BD Biosciences) and a flow cytometer FACSCanto II manufactured by BD Biosciences.

Evaluation criteria were as follows.
[Evaluation Criteria]

A: A indicates a leukocyte removing performance of less than 5.0, suggesting high capability to remove leukocyte.

B: B indicates a leukocyte removing performance of 5.0 or more and less than 5.5, suggesting good capability to remove leukocyte.

C: C indicates a leukocyte removing performance of 5.5 or more, suggesting poor capability to remove leukocyte.

(Filtration Time)

In the above-mentioned leukocyte removing performance test, the filtration time (minute) was defined as the length of time (minute) from the point when the erythrocyte preparation was allowed to start flowing through the blood processing filter to the point when a mass increase of the recovery bag for the filtered erythrocyte preparation stopped. The point when a mass increase of the recovery bag stopped refers to the point of time when the mass change of the recovery bag reached 0.1 g or less, the mass change being determined by measuring the mass of the recovery bag every minute from the start of filtration. In the present example, the last one minute for determination in which the mass increase stopped was included in the filtration time when calculated.

Evaluation criteria were as follows.
[Evaluation Criteria]

A: A indicates a filtration time of less than 20 minutes, suggesting outstanding shortening of the filtration time.

B: B indicates a filtration time of more than 20 minutes and 24 minutes or less, suggesting good shortening of the filtration time.

C: C indicates a filtration time of more than 24 minutes, suggesting not outstanding shortening of the filtration time.

Examples 1 to 16, Comparative Examples 1 to 7, 9

Provided were the number of sheets, shown in Table 1 and Table 2, of polybutylene terephthalate (hereinafter, abbreviated as "PBT") nonwoven fabrics having a basis weight of 93 (g/$m^2$), an airflow resistance per unit basis weight of 0.03 (kPa·s·m/g), and a CWST of 95 (mN/m) as the filter material A and PBT nonwoven fabrics having a basis weight of 90 (g/$m^2$), an airflow resistance per unit basis weight of 0.06 (kPa·s·m/g), and CWST of 96 (mN/m) as the filter material B, and all of the filter material A and all of the filter material B were laminated in this order from the upstream side to make a filtration medium as a laminated product.

This filtration medium was sandwiched between 2 sheets of flexible vinyl chloride resin having a port serving as a blood inlet or outlet, and the filtration medium and the flexible sheets were welded along the margins thereof using a high frequency welding machine to integrate them thereby to make a blood processing filter having an effective filtration area of 43 $cm^2$. After applying high-pressure steam sterilization to the blood processing filter at 115° C. for 59 minutes, the above-mentioned leukocyte removing performance test was carried out.

Examples 17, 18

The same procedure as in Example 1 was carried out, except that PBT nonwoven fabrics having a basis weight of 93 (g/$m^2$), a CWST of 95 (mN/m), and an airflow resistance per unit basis weight of 0.01 (kPa·s·m/g) or 0.04 (kPa·s·m/g) were used as the filter material A.

Example 19

The same procedure as in Example 1 was carried out, except that PBT nonwoven fabrics having a basis weight of 90 (g/$m^2$), a CWST of 96 (mN/m), and an airflow resistance per unit basis weight of 0.08 (kPa·s·m/g) were used as the filter material B.

Example 20

The same procedure as in Example 1 was carried out, except that PBT nonwoven fabrics having a basis weight of 90 (g/m$^2$), a CWST of 88 (mN/m), and an airflow resistance per unit basis weight of 0.06 (kPa·s·m/g) were used as the filter material B.

Example 21

The same procedure as in Example 1 was carried out, except that PBT nonwoven fabrics having a basis weight of 90 (g/m$^2$), a CWST of 80 (mN/m), and an airflow resistance per unit basis weight of 0.06 (kPa·s·m/g) were used as the filter material B.

Examples 22 to 25

The same procedure as in Example 1 was carried out, except that PBT nonwoven fabrics having a basis weight of 93 (g/m$^2$), a CWST of 95 (mN/m), and an airflow resistance per unit basis weight of 0.02 (kPa·s·m/g) were used as the filter material A.

Examples 26 to 29

The same procedure as in Example 1 was carried out, except that PBT nonwoven fabrics having a basis weight of 93 (g/m$^2$), a CWST of 95 (mN/m), and an airflow resistance per unit basis weight of 0.04 (kPa·s·m/g) were used as the filter material A.

Comparative Example 8

The same procedure as in Example 5 was carried out, except that all of the filter material B and all of the filter material A were laminated in this order from the upstream side to make a filtration medium as a laminated product.

Comparative Example 10

The same procedure as in Example 1 was carried out, except that polybutylene terephthalate (hereinafter, abbreviated as "PBT") nonwoven fabrics having a basis weight of 90 (g/m$^2$), an airflow resistance per unit basis weight of 0.06 (kPa·s·m/g), and a CWST of 95 (mN/m) as the filter material A and PBT nonwoven fabrics having a basis weight of 90 (g/m$^2$), an airflow resistance per unit basis weight of 0.06 (kPa·s·m/g), and a CWST of 80 (mN/m) as the filter material B were used.

The leukocyte removing performances and the filtration times determined in Examples 1 to 29 and Comparative Examples 1 to 10 are shown in Table 1 and Table 2, respectively. From the comparison in terms of these two performances between Examples and Comparative Examples that have a comparable airflow resistance of the filtration medium, it is understood that the blood filter of the present invention can achieve both of these two performances.

TABLE 1

| Item | Filter material | Unit | Example 1 | Example 2 | Example 3 | Example 4 | Example 5 | Example 6 | Example 7 | Example 8 |
|---|---|---|---|---|---|---|---|---|---|---|
| Basis weight | A | g/m$^2$ | 93 | 93 | 93 | 93 | 93 | 93 | 93 | 93 |
|  | B |  | 90 | 90 | 90 | 90 | 90 | 90 | 90 | 90 |
| Number of sheets of each filter material | A | Sheet | 2 | 4 | 10 | 14 | 7 | 2 | 4 | 10 |
|  | B |  | 10 | 9 | 5 | 3 | 8 | 12 | 11 | 7 |
| Airflow resistance per unit basis weight | A | kPa·s·m/g | 0.03 | 0.03 | 0.03 | 0.03 | 0.03 | 0.03 | 0.03 | 0.03 |
|  | B |  | 0.06 | 0.06 | 0.06 | 0.06 | 0.06 | 0.06 | 0.06 | 0.06 |
|  | A/B | — | 0.57 | 0.57 | 0.57 | 0.57 | 0.57 | 0.57 | 0.57 | 0.57 |
| Airflow resistance of each layer | A | kPa·s·m/ layer | 6.2 | 12.4 | 31.1 | 43.5 | 21.8 | 6.2 | 12.4 | 31.1 |
|  | B |  | 52.2 | 47.0 | 26.1 | 15.7 | 41.8 | 62.7 | 57.4 | 36.5 |
| CWST | A | mN/m | 95 | 95 | 95 | 95 | 95 | 95 | 95 | 95 |
|  | B |  | 96 | 96 | 96 | 96 | 96 | 96 | 96 | 96 |
| Airflow resistance of filtration medium |  | kPa·s/m | 58.43 | 59.42 | 57.20 | 59.19 | 63.53 | 68.87 | 69.87 | 67.64 |
| Count of residual leukocyte |  | Log | 5.3 | 4.6 | 4.9 | 5.4 | 4.5 | 5.3 | 4.8 | 4.6 |
|  | Evaluation | — | B | A | A | B | A | B | A | A |
| Filtration time |  | min | 15.7 | 14.8 | 14.5 | 14.3 | 14.4 | 22 | 17.5 | 16.2 |
|  | Evaluation | — | A | A | A | A | A | B | A | A |

| Item | Filter material | Unit | Example 9 | Example 10 | Example 11 | Example 12 | Example 13 | Example 14 | Example 15 |
|---|---|---|---|---|---|---|---|---|---|
| Basis weight | A | g/m$^2$ | 93 | 93 | 93 | 93 | 93 | 93 | 93 |
|  | B |  | 90 | 90 | 90 | 90 | 90 | 90 | 90 |
| Number of sheets of each filter material | A | Sheet | 14 | 4 | 8 | 14 | 11 | 2 | 8 |
|  | B |  | 5 | 12 | 9 | 6 | 8 | 15 | 11 |
| Airflow resistance per unit basis weight | A | kPa·s·m/g | 0.03 | 0.03 | 0.03 | 0.03 | 0.03 | 0.03 | 0.03 |
|  | B |  | 0.06 | 0.06 | 0.06 | 0.06 | 0.06 | 0.06 | 0.06 |
|  | A/B | — | 0.57 | 0.57 | 0.57 | 0.57 | 0.57 | 0.57 | 0.57 |
| Airflow resistance of each layer | A | kPa·s·m/ layer | 43.5 | 12.4 | 24.9 | 43.5 | 34.2 | 6.2 | 24.9 |
|  | B |  | 26.1 | 62.7 | 47.0 | 31.3 | 41.8 | 78.3 | 57.4 |

TABLE 1-continued

| Item | Filter material | Unit | | | | | | | |
|---|---|---|---|---|---|---|---|---|---|
| CWST | A | mN/m | 95 | 95 | 95 | 95 | 95 | 95 | 95 |
|  | B |  | 96 | 96 | 96 | 96 | 96 | 96 | 96 |
| Airflow resistance of filtration medium |  | kPa·s/m | 69.63 | 75.09 | 71.86 | 74.85 | 75.97 | 84.53 | 82.30 |
| Count of residual leukocyte |  | Log | 5.2 | 5.1 | 4.5 | 4.8 | 4.5 | 5.3 | 4.8 |
|  | Evaluation | — |  | B | B | A | A | A | B | A |
| Filtration time |  | min | 16.1 | 19 | 17.5 | 17.2 | 18.4 | 24 | 19.8 |
|  | Evaluation | — |  | A | A | A | A | A | B | A |

| Item | Filter material | Unit | Example 16 | Example 17 | Example 18 | Example 19 | Example 20 | Example 21 | Example 22 | Example 23 |
|---|---|---|---|---|---|---|---|---|---|---|
| Basis weight | A | g/m² | 93 | 93 | 93 | 93 | 93 | 93 | 93 | 93 |
|  | B |  | 90 | 90 | 90 | 90 | 90 | 90 | 90 | 90 |
| Number of sheets of each filter material | A | Sheet | 14 | 14 | 6 | 7 | 4 | 4 | 7 | 16 |
|  | B |  | 7 | 9 | 8 | 6 | 11 | 11 | 9 | 7 |
| Airflow resistance per unit basis weight | A | kPa·s·m/g | 0.03 | 0.01 | 0.04 | 0.03 | 0.03 | 0.03 | 0.02 | 0.02 |
|  | B |  | 0.06 | 0.06 | 0.06 | 0.08 | 0.06 | 0.06 | 0.06 | 0.06 |
|  | A/B | — | 0.57 | 0.17 | 0.69 | 0.42 | 0.57 | 0.57 | 0.34 | 0.34 |
| Airflow resistance of each layer | A | kPa·s·m/layer | 43.5 | 13.0 | 22.3 | 21.8 | 12.4 | 12.4 | 13.0 | 29.7 |
|  | B |  | 36.5 | 47.0 | 41.8 | 43.0 | 57.4 | 57.4 | 47.0 | 36.5 |
| CWST | A | mN/m | 95 | 95 | 95 | 95 | 95 | 95 | 95 | 95 |
|  | B |  | 96 | 96 | 96 | 96 | 88 | 80 | 96 | 96 |
| Airflow resistance of filtration medium |  | kPa·s/m | 80.07 | 59.99 | 64.06 | 64.80 | 69.87 | 69.87 | 59.99 | 66.28 |
| Count of residual leukocyte |  | Log | 4.6 | 4.9 | 4.6 | 4.5 | 4.6 | 4.5 | 4.9 | 4.8 |
|  | Evaluation | — | A | A | A | A | A | A | A | A |
| Filtration time |  | min | 19.8 | 15.2 | 15.8 | 16.2 | 17.5 | 17.5 | 16.2 | 18.1 |
|  | Evaluation | — | A | A | A | A | A | A | A | A |

| Item | Filter material | Unit | Example 24 | Example 25 | Example 26 | Example 27 | Example 28 | Example 29 |
|---|---|---|---|---|---|---|---|---|
| Basis weight | A | g/m² | 93 | 93 | 93 | 93 | 93 | 93 |
|  | B |  | 90 | 90 | 90 | 90 | 90 | 90 |
| Number of sheets of each filter material | A | Sheet | 16 | 7 | 4 | 8 | 8 | 4 |
|  | B |  | 5 | 10 | 9 | 7 | 5 | 10 |
| Airflow resistance per unit basis weight | A | kPa·s·m/g | 0.02 | 0.02 | 0.04 | 0.04 | 0.04 | 0.04 |
|  | B |  | 0.06 | 0.06 | 0.06 | 0.06 | 0.06 | 0.06 |
|  | A/B | — | 0.34 | 0.34 | 0.69 | 0.69 | 0.69 | 0.69 |
| Airflow resistance of each layer | A | kPa·s·m/layer | 29.7 | 13.0 | 14.9 | 29.7 | 29.7 | 14.9 |
|  | B |  | 26.1 | 52.2 | 47.0 | 36.5 | 26.1 | 52.2 |
| CWST | A | mN/m | 95 | 95 | 95 | 95 | 95 | 95 |
|  | B |  | 96 | 96 | 96 | 96 | 96 | 96 |
| Airflow resistance of filtration medium |  | kPa·s/m | 55.83 | 65.22 | 61.85 | 66.28 | 55.83 | 67.07 |
| Count of residual leukocyte |  | Log | 4.9 | 4.9 | 4.5 | 4.6 | 4.6 | 4.7 |
|  | Evaluation | — | A | A | A | A | A | A |
| Filtration time |  | min | 16.4 | 18.5 | 15.8 | 16.0 | 15.9 | 16.3 |
|  | Evaluation | — | A | A | A | A | A | A |

TABLE 2

| Item | Filter material | Unit | Comparative Example 1 | Comparative Example 2 | Comparative Example 3 | Comparative Example 4 | Comparative Example 5 |
|---|---|---|---|---|---|---|---|
| Basis weight | A | g/m² | 93 | 93 | 93 | 93 | 93 |
|  | B |  | 90 | 90 | 90 | 90 | 90 |
| Number of sheets of each filter material | A | Sheet | 2 | 14 | 0 | 0 | 0 |
|  | B |  | 9 | 2 | 11 | 13 | 16 |
| Airflow resistance per unit basis weight | A | kPa·s·m/g | 0.03 | 0.03 | 0.03 | 0.03 | 0.03 |
|  | B |  | 0.06 | 0.06 | 0.06 | 0.06 | 0.06 |
|  | A/B | — | 0.57 | 0.57 | 0.57 | 0.57 | 0.57 |

TABLE 2-continued

|   |   |   |   |   |   |   |   |
|---|---|---|---|---|---|---|---|
| Airflow resistance of each layer | A<br>B | kPa·s·m/<br>layer | 6.2<br>47.0 | 43.5<br>10.4 | 0.0<br>57.4 | 0.0<br>67.9 | 0.0<br>83.5 |
| CWST | A<br>B | mN/m | 95<br>96 | 95<br>96 | 95<br>96 | 95<br>96 | 95<br>96 |
| Airflow resistance of filtration medium |  | kPa·s/m | 53.21 | 53.97 | 57.43 | 67.87 | 83.53 |
| Count of residual leukocyte |  | Log | 6.2 | 6.2 | 6.4 | 6.2 | 6.2 |
|  | Evaluation | — | C | C | C | C | C |
| Filtration time |  | min | 14.5 | 12.9 | 16.2 | 25 | 32 |
|  | Evaluation | — | A | A | A | C | C |

| Item | Filter material | Unit | Comparative Example 6 | Comparative Example 7 | Comparative Example 8 | Comparative Example 9 | Comparative Example 10 |
|---|---|---|---|---|---|---|---|
| Basis weight | A<br>B | g/m² | 93<br>90 | 93<br>90 | 90<br>93 | 93<br>90 | 90<br>90 |
| Number of sheets of each filter material | A<br>B | Sheet | 2<br>16 | 14<br>8 | 8<br>7 | 1<br>11 | 7<br>6 |
| Airflow resistance per unit basis weight | A<br>B<br>A/B | kPa·s·m/g | 0.03<br>0.06<br>0.57 | 0.03<br>0.06<br>0.57 | 0.06<br>0.03<br>1.74 | 0.03<br>0.06<br>0.57 | 0.06<br>0.06<br>1.00 |
| Airflow resistance of each layer | A<br>B | kPa·s·m/<br>layer | 6.2<br>83.5 | 43.5<br>41.8 | 41.8<br>21.8 | 3.1<br>57.4 | 36.5<br>31.3 |
| CWST | A<br>B | mN/m | 95<br>96 | 95<br>96 | 95<br>96 | 95<br>96 | 95<br>80 |
| Airflow resistance of filtration medium |  | kPa·s/m | 89.75 | 85.29 | 63.53 | 60.54 | 67.87 |
| Count of residual leukocyte |  | Log | 5.4 | 4.9 | 6.0 | 5.7 | 6.3 |
|  | Evaluation | — | B | A | C | C | C |
| Filtration time |  | min | 28 | 27.2 | 24.5 | 17 | 26.2 |
|  | Evaluation | — | C | C | C | A | C |

The present application claims a priority benefit to a Japanese patent application filed on Aug. 30, 2018 (Japanese Patent Application No. 2018-161285), the contents of which are incorporated herein by reference.

INDUSTRIAL APPLICABILITY

The blood processing filter of the present invention can be used as a blood processing filter for removing undesirable components such as aggregates and leukocytes from a liquid containing blood components or blood.

In particular, the present blood processing filter can be preferably used as a disposable blood processing filter used for the purpose of removing microaggregates and leukocytes, which are likely to cause side effects, from whole blood preparations, erythrocyte preparations, thrombocyte preparations, blood plasma preparations and the like for blood transfusion.

The invention claimed is:

1. A blood processing filter comprising:
a container having 2 ports respectively functioning as an inlet for a liquid to be processed and as an outlet for the processed liquid, and
a filtration medium filled in the container,
wherein an airflow resistance of the filtration medium is 55.0 kPa·s/m or more and less than 85.0 kPa·s/m,
the filtration medium comprises a filter material A having an airflow resistance per unit basis weight of 0.01 kPa·s·m/g or more and less than 0.04 kPa·s·m/g and a filter material B having an airflow resistance per unit basis weight of 0.04 kPa·s·m/g or more,
at least a part of the filter material A is disposed on a side closer to the inlet for a liquid to be processed than the filter material B, and
a sum of the airflow resistances of the filter material A that is disposed on the side closer to the inlet for a liquid to be processed than the filter material B is 6.0 kPa·s/m or more.

2. The blood processing filter according to claim 1, comprising: a plurality of kinds of the filter material A,
wherein a filter material having the lowest airflow resistance per unit basis weight among the plurality of kinds of the filter material A is designated as a filter material A', at least a part of the filter material A' is disposed on the side closer to the inlet for a liquid to be processed than the filter material B, and
a sum of the airflow resistances of the filter material A' that is disposed on the side closer to the inlet for a liquid to be processed than the filter material B is 6.0 kPa·s/m or more.

3. The blood processing filter according to claim 1, wherein the airflow resistance of the filtration medium is 55.0 kPa·s/m or more and less than 70.0 kPa·s/m, and
the sum of the airflow resistances of the filter material A that is disposed on the side closer to the inlet for a liquid to be processed than the filter material B is 12.0 kPa·s/m or more and less than 32.0 kPa·s/m.

4. The blood processing filter according to claim 1, wherein a critical wet surface tension (CWST) of the filter material B is 80 mN/m or more and 90 mN/m or less.

5. The blood processing filter according to claim 1, wherein the airflow resistance of the filtration medium is 70.0 kPa·s/m or more and less than 85.0 kPa·s/m, and
the sum of the airflow resistances of the filter material A that is disposed on the side closer to the inlet for a liquid to be processed than the filter material B is 24.0 kPa·s/m or more.

6. A method for producing the blood processing filter according to claim 1, comprising:
   providing a filter material A and a filter material B, and laminating at least a part of the filter material A to the filter material B to make a laminated product.

* * * * *